United States Patent [19]

Bielefeldt et al.

[11] Patent Number: 5,093,522

[45] Date of Patent: Mar. 3, 1992

[54] CARBOXYLIC ACID HALIDES CONTAINING TRIFLUOROMETHYL GROUPS AND A PROCESS FOR THEIR PREPARATION

[75] Inventors: Dietmar Bielefeldt, Ratingen; Heinz Ziemann, Leichlingen, both of Fed. Rep. of Germany

[73] Assignee: Bayer Aktiengesellschaft, Leverkusen, Fed. Rep. of Germany

[21] Appl. No.: 581,836

[22] Filed: Sep. 12, 1990

[30] Foreign Application Priority Data

Oct. 5, 1989 [DE] Fed. Rep. of Germany ....... 3933223

[51] Int. Cl.$^5$ .............................................. C07C 51/58
[52] U.S. Cl. ................................... 562/848; 562/849; 562/840; 562/851
[58] Field of Search ................ 562/849, 848, 840, 851

[56] References Cited

FOREIGN PATENT DOCUMENTS 2417922 4/1974 Fed. Rep. of Germany .

*Primary Examiner*—Jose G. Dees
*Assistant Examiner*—Keith MacMillan
*Attorney, Agent, or Firm*—Sprung Horn Kramer & Woods

[57] ABSTRACT

The present invention relates to new carboxylic acid halides containing trifluoromethyl groups, of the formula (I)

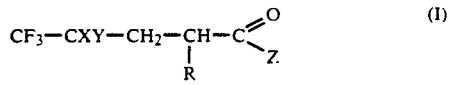

in which the symbols used have the meanings given in the description, a process for their preparation by reaction of perhalogenoalkanes with carbon monoxide and an olefin and their use for the preparation of textile auxiliaries.

6 Claims, No Drawings

CARBOXYLIC ACID HALIDES CONTAINING TRIFLUOROMETHYL GROUPS AND A PROCESS FOR THEIR PREPARATION

The present invention relates to new carboxylic acid halides containing trifluoromethyl groups and their preparation from perhalogenated hydrocarbons, olefins and carbon monoxide.

Carboxylic acid halides containing trichloromethyl groups are known. They are used, for example, as intermediate products for the preparation of fluorinated carboxylic acids and salts thereof, the products being surfactants and surface-active agents. They can also be used as intermediate products for the preparation of oleophobic, hydrophobic and dirt-repellent agents for textile treatment (see U.S. Pat. No. 4,221,734 and Ullmann, Encyklopädie der technischen Chemie, (Encyclopaedia of Industrial Chemistry), volume 22, page 500 (1982)).

Compounds containing trifluoromethyl groups are usually prepared from the corresponding compounds containing trichloromethyl groups by chlorine/fluorine exchange using hydrofluoric acid. The disadvantage of this process is that the fluorination must be carried out individually to a higher processing stage, which requires particular technical expenditure.

New carboxylic acid halides containing trifluoromethyl groups, of the formula (I)

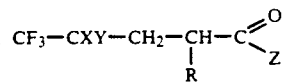   (I)

in which
  R represents hydrogen or saturated or unsaturated, straight-chain or branched $C_1$- to $C_{10}$-alkyl,
  Z represents fluorine, chlorine, bromine or iodine,
  X represents fluorine, chlorine, bromine, iodine or trifluoromethyl and
  Y represents fluorine, chlorine, bromine or iodine, and in the case where Z=chlorine, X and Y do not represent fluorine, have now been found.

Preferably,
  R represents hydrogen or saturated or unsaturated straight-chain $C_1$- to $C_3$-alkyl,
  Z represents chlorine, bromine or iodine,
  X represents fluorine, chlorine or trifluoromethyl and
  Y represents fluorine or chlorine,
wherein, in the case where Z=chlorine, X and Y do not simultaneously represent fluorine.

Particularly preferred carboxylic acid halides of the formula (I) are:
4,4,4-trifluoro-3,3-dichloro-n-pentanoyl chloride,
4,4,4-trifluoro-3,3-dichloro-n-pentanoyl bromide and
4,4,4-trifluoro-3,3-dichloro-1methyl-n-pentanoyl chloride.

An especially preferred carboxylic acid halide of the formula (I) is 4,4,4-trifluoro-3,3-dichloro-n-pentanoyl chloride.

A process has furthermore been found for the preparation of carboxylic acid halides containing trifluoromethyl groups, of the formula (I)

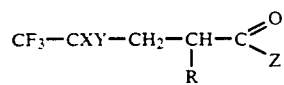   (I)

in which
  R represents hydrogen or saturated or unsaturated, straight-chain or branched $C_1$- to $C_{10}$-alkyl,
  Z represents fluorine, chlorine, bromine or iodine,
  X represents fluorine, chlorine, bromine, iodine or trifluoromethyl and
  Y represents fluorine, chlorine, bromine or iodine, and in the case where Z=chlorine, X and Y do not simultaneously represent fluorine,
which is characterized in that a perhalogenoalkane of the formula (II)

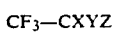   (II)

in which X, Y and Z have the meaning given in the case of formula (I), is reacted with carbon monoxide and an olefin of the formula (III)

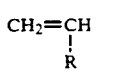   (III)

in which
  R has the meaning given in the case of formula (I), with the addition of a catalyst containing an element of sub-group VI to VIII of the Periodic Table of the Elements and carbonyl groups.

In the formulae (II) and (III), preferably,
  R represents hydrogen or saturated or unsaturated straight-chain $C_1$- to $C_3$-alkyl,
  Z represents chlorine, bromine or iodine,
  Y represents fluorine, chlorine or trifluoromethyl and
  Y represents fluorine or chlorine,
wherein, in the case where Z=chlorine, X and Y do not represent fluorine.

Particularly preferred combinations are
  R=hydrogen, X=Y=Z=chlorine,
  R=hydrogen, Z=bromine, X=Y=chlorine,
  R=hydrogen, Z=iodine, X=Y=fluorine,
  R=hydrogen, Z=iodine, X=trifluoromethyl, Y=fluorine and
  R=methyl, X=Y=Z=chlorine.

Especially preferred combinations are
  R=hydrogen, X=Y=Z=chlorine and
  R=hydrogen, Z=iodine, X=Y=fluorine.

The perhalogenoalkanes of the formula (II) to be employed are commercial products or materials which can be prepared in a simple and known manner.

The carbon monoxide required can be employed in commercially available qualities.

The catalyst required necessarily contains an element of sub-group VI to VIII of the Periodic Table of the Elements and carbonyl groups. Preferred elements of sub-group VI to VIII are molybdenum, cobalt, iron, ruthenium, rhodium, osmium and iridium. The metal carbonyls can be mono- or polynuclear compounds.

If appropriate, metal carbonyls which are suitable catalysts for the process according to the invention can contain, in addition to carbonyl groups, one or more other ligands, for example hydrogen atoms, halogen atoms, phosphorus-trialkyls, phosphorus-triaryls and-/or cyclopentadiene.

The following metal carbonyls are preferred:

| | |
|---|---|
| $Ni(CO)_4$ | $Rh_6(CO)_{16}$ |
| $Co_2(CO)_8$ | $Co_2(CO)_6[P(C_4H_9)_3]_2$ |
| $Rh_4(CO)_{12}$ | $HRh(CO)[P(C_6H_5)_3]_3$ |
| $Ru_3(CO)_{12}$ | $Ir(CO)[P(C_6H_5)_3]_2Cl$ |
| $Os_3(CO)_{12}$ | $Cp_2Fe_2(CO)_4$ |
| $Ir_4(CO)_{12}$ | $Cp_2Mo_2(CO)_6$ |
| | (Cp = cyclopentadiene). |

In addition to the metal carbonyls described above, a co-catalyst can be employed if appropriate. This can be, for example, a palladium salt, preferably $PdCl_2$, or tin-(II) chloride.

Both carbon monoxide and the perhalogenoalkane of the formula (II) are preferably employed in a molar excess relative to the olefin of the formula (III). For example, it is possible to employ 3 or more mol of carbon monoxide and 3 or more mol of the perhalogenoalkane of the formula (II) per mol of the olefin of the formula (III).

The metal carbonyl catalyst can be employed, for example, in an amount of 0.01 to 100 mmol per mol of the olefin of the formula (III). This amount is preferably 0.1 to 10 mmol.

If appropriate, the co-catalyst can be employed in an amount of, for example, 0 to 100 mmol per mol of olefin of the formula (III).

The reaction temperature can be varied within wide limits. Preferably, the reaction is started at relatively low temperatures, for example at $-20°$ to $+50°$ C., the temperature is increased in the course of the reaction and the reaction is brought to completion, for example, at 70° to 200° C.

If appropriate, the reaction can be carried out in the presence of an inert solvent. Preferably, however, no solvent is employed.

Since the starting substances and reaction products are in some cases gaseous at the reaction temperatures under normal pressure, the process according to the invention is in general carried out under pressure. The metering of the amounts of carbon monoxide and olefin of the formula (III) can be effected by establishing and if appropriate maintaining certain (partial) pressures in the reaction vessel. It should in general be possible to operate the reaction vessels, for example autoclaves, under pressures up to 300 bar.

The reaction according to the invention has in general ended when no further carbon monoxide and no further olefin of the formula (III) is reacted. This can be seen, for example, by the fact that the pressure in the reaction vessel (at constant temperature) no longer changes.

The reaction mixture present after the end of the reaction can be worked up, for example, by a procedure in which it is cooled and let down, and excess starting substances, if appropriate the solvent used, the carboxylic acid of the formula (I) prepared and if appropriate by-products are distilled off in succession. A residue of low volatility, which essentially contains the catalyst employed, then in general remains. If appropriate, this can be used again for subsequent batches.

With the new carboxylic acid halides of the formula (I) containing trifluoromethyl groups, new intermediate products are provided with which, if appropriate after conversion into the corresponding free acids or the corresponding aldehydes, esters or amides in a manner which is known per se, textile treatment agents can be prepared which are previously inaccessible variants of the types known from perfluoroalkanecarboxylic acids or -sulphonic acids. Such textile treatment agents can be prepared by processes analogous to those described in the literature (see, for example, Ullmann, Encyclopädie der technischen Chemie (Encyclopaedia of Industrial Chemistry), volume 11, page 646 et seq. (1976)). The process according to the invention for the preparation of carboxylic acid halides containing trifluoromethyl groups has the advantage that commercial products containing trifluoromethyl groups and easily accessible perhalogenoalkanes can be used as starting substances and individual fluorination to a higher processing stage can be avoided. It is also surprising that the 3-component reaction according to the invention (perhalogenoalkane + olefin + carbon monoxide) proceeds with good yields, since such reactions are in general not very probable because of their complicated kinetics.

EXAMPLES

EXAMPLE 1

Preparation of $CF_3—CCl_2—CH_2—CH_2—COCl$

A gas mixture of 20 bar of ethylene and 100 bar of carbon monoxide was forced into a solution of 2 g of $PdCl_2$ and 2.3 g of $Co_2(CO)_8$ in 1000 ml (8.6 mol) of $CF_3CCl_3$ in a 3 l stainless steel autoclave at 23° C. The mixture was heated stepwise to 140° C. and the pressure was kept constant by subsequently forcing in the gas mixture. The end of the reaction was reached after 15 hours, with the end of the uptake of gas. After cooling and releasing the pressure, the resulting reaction mixture was subjected to fractional distillation. The yield of 4,4,4-trifluoro-3,3-dichloro-n-butyryl chloride was 320 g. The boiling point was 91° to 95° C. under 60 mbar. The IR spectrum showed characteristic absorptions at 1800 cm$^{-1}$ (CO) and 1235, 1205 and 1190 cm$^{-1}$ (CF$_3$). The mass spectrum gave a value for m$^+$/e of 242.

EXAMPLE 2

Preparation of

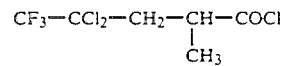

The procedure was analogous to Example 1, but instead of 20 bar of ethylene, 10 bar of propene were forced in. The end of the reaction was reached after 20 hours.

The yield of 4,4,4-trifluoro-3,3-dichloro-1-methyl-n-butyryl chloride was 105 g. The boiling point was 105° to 107° C. under 150 mbar. The IR spectrum had a characteristic absorption at 1785 cm$^{-1}$ (CO).

What is claimed is:

1. The carboxylic acid halides containing trifluoromethyl groups, of the formula

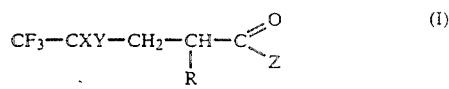

which are
4,4,4-trifluoro-3,3-dichloro-n-pentanoyl chloride,
4,4,4-trifluoro-3,3-dichloro-n-pentanoyl bromine and
4,4,4-trifluoro-3,3-dichloro-1-methyl-n-pentanoyl chloride.

2. A process for the preparation of carboxylic acid halides containing trifluoromethyl groups, of the formula (I)

$$CF_3-CXY-CH_2-\underset{R}{CH}-C\underset{Z}{\overset{O}{\lessgtr}} \qquad (I)$$

in which
R represents hydrogen or saturated or unsaturated, straight-chain or branched $C_1$- to $C_{10}$-alkyl,
Z represents fluorine, chlorine, bromine or iodine,
X represents fluorine, chlorine, bromine, iodine or trifluoromethyl and
Y represents fluorine, chlorine, bromine or iodine, and in the case where Z=chlorine, X and Y do not simultaneously represent fluorine, in which a perhalogenoalkane of the formula (II)

$$CF_3-CXYZ \qquad (II)$$

in which X, Y and Z have the meaning given in the case of formula (I), is reacted with carbon monoxide and an olefin of the formula (III)

$$CH_2=\underset{R}{CH} \qquad (III)$$

in which
R has the meaning given in the case of formula (I), with the addition of a catalyst containing an element of sub-group VI to VIII of the Periodic Table of the Elements and carbonyl groups.

3. The process of claim 2, in which the catalyst contains molybdenum, cobalt, iron, ruthenium, rhodium, osmium or iridium.

4. The process of claim 2, in which the catalyst is

| | |
|---|---|
| $Ni(CO)_4$ | $Rh_6(CO)_{16}$ |
| $Co_2(CO)_8$ | $Co_2(CO)_6[P(C_4H_9)_3]_2$ |
| $Rh_4(CO)_{12}$ | $HRh(CO)[P(C_6H_5)_3]_3$ |
| $Ru_3(CO)_{12}$ | $Ir(CO)[P(C_6H_5)_3]_2Cl$ |
| $Os_3(CO)_{12}$ | $Cp_2Fe_2(CO)_4$ or |
| $Ir_4(CO)_{12}$ | $Cp_2Mo_2(CO)_6$ |
| | (Cp = cyclopendiene). |

5. The process of claim 2, in which a palladium salt or tin(II) chloride is employed as a co-catalyst.

6. The process of claim 2, in which carbon monoxide and the perhalogenoalkane of the formula (II) are employed in a molar excess relative to the olefin of the formula (III).

* * * * *

UNITED STATES PATENT AND TRADEMARK OFFICE
CERTIFICATE OF CORRECTION

PATENT NO. : 5,093,522

DATED : March 3, 1992

INVENTOR(S) : Bielefeldt et al.

It is certified that error appears in the above-identified patent and that said Letters Patent is hereby corrected as shown below:

Col. 6, line 21   Delete " cyclopendiene " and substitute -- cyclopentadiene --

Signed and Sealed this

Second Day of November, 1993

Attest:

BRUCE LEHMAN

Attesting Officer    Commissioner of Patents and Trademarks